United States Patent
Stühle et al.

(10) Patent No.: US 11,234,579 B2
(45) Date of Patent: Feb. 1, 2022

(54) RESECTOSCOPE AND ELECTRODE ASSEMBLY THEREFOR

(71) Applicant: OLYMPUS WINTER & IBE GmbH, Hamburg (DE)

(72) Inventors: Sebastian Stühle, Haltern am See (DE); Nils Kapfermann, Hamburg (DE); Thomas Freitag, Hamburg (DE); Andreas Kaiser, Hamburg (DE); Christian Brockmann, Hollenstedt (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 324 days.

(21) Appl. No.: 16/078,908

(22) PCT Filed: Mar. 7, 2017

(86) PCT No.: PCT/EP2017/055263
§ 371 (c)(1),
(2) Date: Aug. 22, 2018

(87) PCT Pub. No.: WO2017/153374
PCT Pub. Date: Sep. 14, 2017

(65) Prior Publication Data
US 2019/0053692 A1    Feb. 21, 2019

(30) Foreign Application Priority Data
Mar. 11, 2016 (DE) ................ 10 2016 204 047.2

(51) Int. Cl.
*A61B 1/00* (2006.01)
*A61B 18/14* (2006.01)
*A61B 18/00* (2006.01)

(52) U.S. Cl.
CPC ........... *A61B 1/00096* (2013.01); *A61B 1/00* (2013.01); *A61B 1/00165* (2013.01);
(Continued)

(58) Field of Classification Search
CPC ....... A61B 1/00096; A61B 1/00; A61B 18/14; A61B 1/00165; A61B 1/00195;
(Continued)

(56) References Cited

U.S. PATENT DOCUMENTS

| 4,116,198 A | 9/1978 | Roos |
| 7,258,691 B2* | 8/2007 | Aue ..................... A61B 18/149 606/1 |

(Continued)

FOREIGN PATENT DOCUMENTS

| CN | 102905635 A | 1/2013 |
| DE | 25 28 543 A1 | 1/1976 |

(Continued)

OTHER PUBLICATIONS

May 12, 2017 International Search Report issued in International Patent Application No. PCT/EP2017/055263.
(Continued)

*Primary Examiner* — Linda C Dvorak
*Assistant Examiner* — Nils A Potter
(74) *Attorney, Agent, or Firm* — Oliff PLC

(57) ABSTRACT

A resectoscope has an elongated shaft tube, an elongated optic arranged therein with a lens at the distal end and an electrode assembly, wherein the electrode assembly in turn includes an electrode arranged at the distal end of the arms of a fork assembly, which are arranged on opposing sides of the lens and are brought together in a transition region to an electrode shaft, wherein the electrode assembly can be extended in the longitudinal direction by a stroke length from a first position, in which the electrode is arranged (Continued)

inside the shaft tube in front of the lens, into a second position in which the arms of the fork assembly protrude out of the shaft tube. The length of the arms of the fork assembly is thereby greater than 1.2 times the stroke length. The electrode assembly is configured correspondingly.

9 Claims, 4 Drawing Sheets

(52) U.S. Cl.
CPC .......... *A61B 1/00195* (2013.01); *A61B 18/14* (2013.01); *A61B 18/149* (2013.01); *A61B 2018/0097* (2013.01); *A61B 2018/00982* (2013.01)

(58) Field of Classification Search
CPC .......... A61B 18/149; A61B 2018/0097; A61B 2018/00982
USPC .......................................................... 606/46
See application file for complete search history.

(56) References Cited

U.S. PATENT DOCUMENTS

| | | | |
|---|---|---|---|
| 2002/0058859 A1 | 5/2002 | Brommersma | |
| 2004/0242959 A1* | 12/2004 | Nosel | A61B 18/149 |
| | | | 600/105 |
| 2008/0009854 A1* | 1/2008 | Yates | A61B 18/1445 |
| | | | 606/42 |
| 2009/0043303 A1 | 2/2009 | Shimomura | |
| 2011/0295066 A1* | 12/2011 | Fan | A61B 1/015 |
| | | | 600/114 |
| 2014/0039486 A1* | 2/2014 | Wootton | A61B 18/1206 |
| | | | 606/33 |

FOREIGN PATENT DOCUMENTS

| | | |
|---|---|---|
| DE | 195 14 552 A1 | 10/1996 |
| DE | 103 45 111 A1 | 5/2005 |
| DE | 10 2014 212 102 A1 | 12/2014 |
| JP | H01-75416 U | 5/1989 |
| JP | H3-295550 A | 12/1991 |
| JP | H09262245 A | 10/1997 |
| JP | 2002095677 A | 4/2002 |
| JP | 2008-246111 A | 10/2008 |

OTHER PUBLICATIONS

Sep. 11, 2018 Translation of International Preliminary Report on Patentability issued in International Application No. PCT/EP2017/055263.

* cited by examiner

RESECTOSCOPE AND ELECTRODE ASSEMBLY THEREFOR

FIELD

The invention relates to a resectoscope and an electrode assembly therefor.

BACKGROUND

Resectoscopes are used in minimally invasive surgical procedures, especially in urology, but also for example in gynecology. At their distal end, they have one or more exposed electrodes for working on tissue. The electrodes can be monopolar or bipolar electrodes. However, it is also possible that the electrode is configured as a free end of a laser fiber.

Resectoscopes generally have an elongate shaft tube for inserting into the body of the patient. A likewise elongate optic is arranged in this shaft tube, and an objective lens is provided at the distal end of the optic. At the other end of the optic, an eyepiece can be provided through which the operator is able to view the operating area in front of the objective lens.

A longitudinally displaceable electrode assembly, with an electrode at the distal end, is likewise arranged in the shaft tube. The electrode assembly can be moved between a retracted state, in which the electrode is arranged inside the shaft tube and directly in front of the objective lens, and a deployed state, in which the electrode protrudes freely from the shaft tube.

In the deployed state, the electrode is located in the viewing field of the optic. To have a good view of the electrode, the operating region is rinsed with a rinsing liquid, in such a way that a constant pressure prevails in the operating area. At the same time, a suitable arrangement of the delivery and aspiration of rinsing liquid is intended to ensure that the region directly in front of the optic remains as far as possible free of dirt obstructing the view, e.g. caused by blood which has leaked out or floating tissue fragments. A crucial requirement for this is the time that is needed until the viewing field of the optic is once again free after becoming dirty.

In order to achieve a flow around the objective lens suitable for rinsing the viewing field free, the rinsing liquid is at least generally delivered directly via the resectoscope. However, the time needed to rinse the viewing field in front of the optic free after soiling is often unsatisfactorily long.

SUMMARY

The object of the invention is to create a resectoscope and an electrode assembly in which the disadvantages of the prior art no longer arise or only arise to a reduced extent.

This object is achieved by a resectoscope according to the main claim and by an electrode assembly for use in such resectoscope according to another independent claim directed to such electrode assembly. Advantageous developments are the subject matter of the dependent claims.

Accordingly, the invention relates to a resectoscope comprising an elongate shaft tube, an elongate optic arranged therein with an objective lens at the distal end and an electrode assembly, wherein the electrode assembly comprises an electrode arranged at the distal end of the arms of a fork assembly, which are arranged on opposite sides of the objective lens and are brought together in a transition region to an electrode shaft, wherein the electrode assembly can be deployed in the longitudinal direction by a stroke length from a first position, in which the electrode is arranged inside the shaft tube in front of the objective lens, to a second position, in which the arms of the fork assembly protrude from the shaft tube, wherein the length of the arms of the fork assembly is greater than 1.2 times the stroke length.

The invention also relates to an electrode assembly for use in a resectoscope (preferably according to the invention), in which the electrode assembly can be deployed in the longitudinal direction by a stroke length, comprising an electrode arranged at the distal end of the arms of a fork assembly, which are brought together in a transition region to an electrode shaft, wherein the length of the arms of the fork assembly is greater than 1.2 times the stroke length.

The invention is based on the recognition that, at least in electrode assemblies which are known from the prior art and which as in the one according to the invention comprise a fork assembly, a transition region and an electrode shaft, but in which the length of the arms of the fork assembly corresponds substantially to the stroke length, the transition regions regularly cause swirling movements in the flowing rinsing liquid in the region directly in front of the objective lens, which is detrimental to the rinsing free of the viewing field. This is because, with a corresponding length of the arms of the fork assembly, the transition region in the deployed state is located directly adjacent to the objective lens and can then cause the undesired swirling movements in the flowing rinsing liquid in the region directly in front of the objective lens.

Since provision is made, according to the invention, that the length of the arms of the fork assembly is considerably greater, namely at least 20% greater, than the stroke length, this has the effect that the transition region of the electrode assembly, even in the deployed state, is arranged sufficiently far from the objective lens of the optic that the transition region causes no swirling movements, or fewer swirling movements compared to the prior art, rinsing free that delay the in the rinsing liquid of the viewing field.

It is preferable if the length of the arms of the fork assembly is greater than 1.3 times the stroke length, preferably greater than 1.4 times the stroke length, more preferably greater than 1.5 times the stroke length. With a suitable length of the arms of the fork assembly, the interference effect of the transition region on the flow in the region of the objective lens can be further reduced. In order to ensure a sufficient stability of the fork assembly, it is preferable if the length of the arms of the fork assembly does not exceed 1.8 times the stroke length.

The transition region of the two arms of the fork assembly to the electrode shaft can be designed in each case with a reflexed airfoil profile. A reflexed airfoil profile is a flowingly curved transition reminiscent of an S shape and leads tangentially from one arm of the fork assembly tangentially to the electrode shaft substantially without an abrupt change of angle. For better guiding of the electrode assembly in the region of the distal end of the shaft tube, a guide element can be provided on the electrode shaft, adjacent to the transition region, which electrode shaft interacts with the optic in such a way that the electrode shaft is guided along the optic. The guide element can be tubular, for example, such that, particularly in the case of a circular cross section of the optic, it engages completely or at least partially around the latter. In the case of partial engagement, the guide element extends over at least 60% of the circumference of the optic.

The advantages of the invention can be realized in different designs of resectoscopes and with different types of rinsing liquid delivery. In particular, however, the advantages of the invention come to bear if the region between the shaft tube and the optic is configured for rinsing liquid delivery. The rinsing liquid in this case flows along the optic, through the region in which the electrode assembly is also located, and emerges at the distal end of the resectoscope. By virtue of the configuration of the electrode assembly according to the invention, flow effects in the stream of rinsing liquid, which may in particular arise on account of the transition region of the electrode assemblies, are situated sufficiently far from the objective lens of the optic, even in the deployed state, to ensure that these flow effects do not cause any swirling movements, or cause only slight swirling, in the region directly in front of the objective lens.

The shaft tube is preferably double-walled, wherein the region between the walls of the shaft tube is configured for rinsing medium discharge. With a suitable configuration, the rinsing liquid can be delivered and also discharged through the resectoscope, such that no separate rinsing liquid delivery devices or rinsing liquid discharge devices need to be provided in an intervention.

The electrode of the electrode assembly is preferably a bipolar electrode. It is more preferably configured as a loop electrode or a flat vaporization electrode.

The stroke length of the resectoscope is preferably 24 mm. The length of the arms of the fork assembly then preferably measures 30 mm to 28 mm, more preferably 32 mm to 34 mm.

For the explanation of the electrode assembly according to the invention, reference is made to the above observations.

BRIEF DESCRIPTION OF THE DRAWINGS

The invention is now described by way of example on the basis of advantageous embodiments and with reference to the attached drawings, in which.

DETAILED DESCRIPTION

Figure 1:
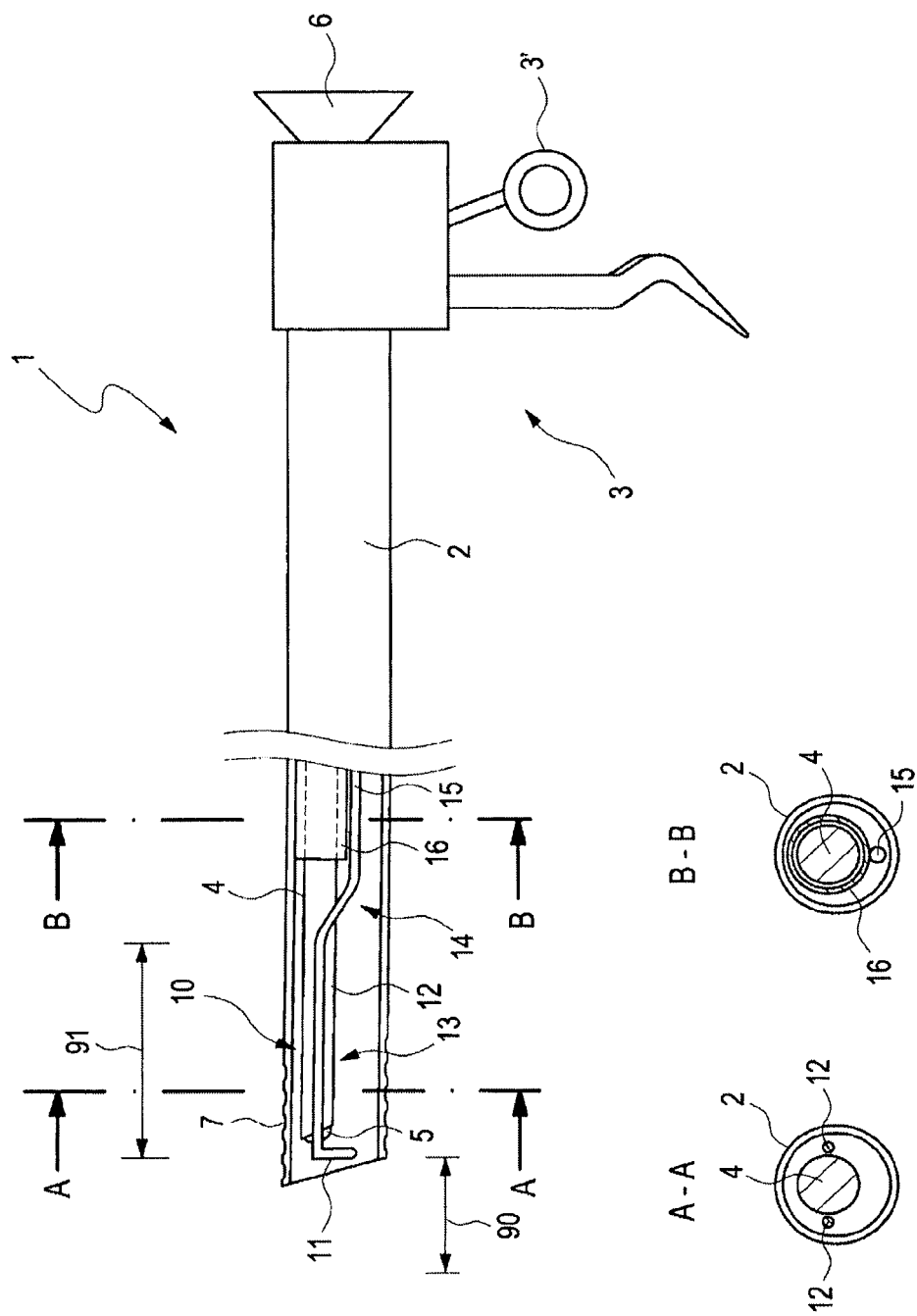
FIG. 1 shows an illustrative embodiment of a resectoscope according to the invention, with the electrode assembly retracted.
Figure 2:
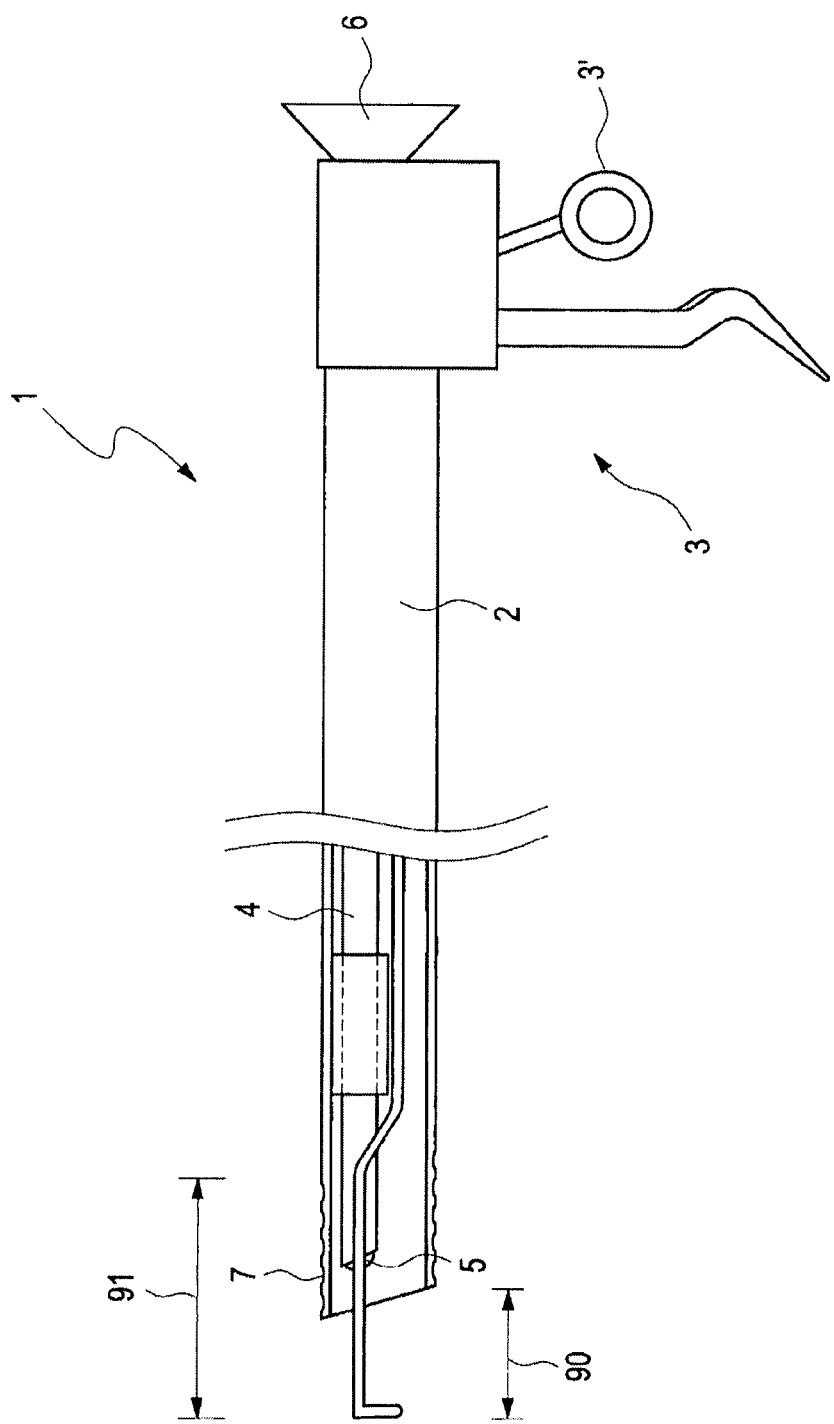
FIG. 2 shows the resectoscope from FIG. 1, with the electrode assembly deployed.

A resectoscope 1 according to the invention is shown in FIGS. 1 and 2. The resectoscope 1 comprises an elongate shaft tube 2, of which the distal end is designed to be inserted into the body of a patient. At its other end, the shaft tube is connected to a grip arrangement 3.

A likewise elongate optic 4 is arranged in the shaft tube 2 and has an objective lens 5 at the distal end. An eyepiece 6 arranged on the grip arrangement 3 is provided at the opposite end of the optic 4.

The region between the optic 4 and the shaft tube 2 is configured for rinsing liquid delivery. Rinsing liquid is delivered here via a port (not shown) on the grip arrangement 3, flows through the space between shaft tube 2 and optic 4 and emerges at the distal end of the shaft tube 2.

The shaft tube 2 is double-walled and, at the distal end, has inlet openings 7 on the outside. Rinsing liquid can be sucked in through these inlet openings 7 and is then conveyed between the two walls of the shaft tube 2 to the grip arrangement 3 and discharged there via a port (not shown).

Since the delivery of the rinsing liquid and the discharge of the rinsing liquid both take place directly through the resectoscope 1, no separate devices need to be provided for the delivery or discharge of rinsing liquid for an intervention.

The resectoscope 1 moreover comprises an electrode assembly 10 which, by way of a grip element 3' of the grip arrangement 3, can be moved between the retracted state shown in FIG. 1 to the deployed state shown in FIG. 2. The length by which the electrode assembly 10 moves between the end points shown in FIGS. 1 and 2 is designated as stroke length 90 and, in the illustrative embodiment shown, measures 24 mm.

Figure 3:
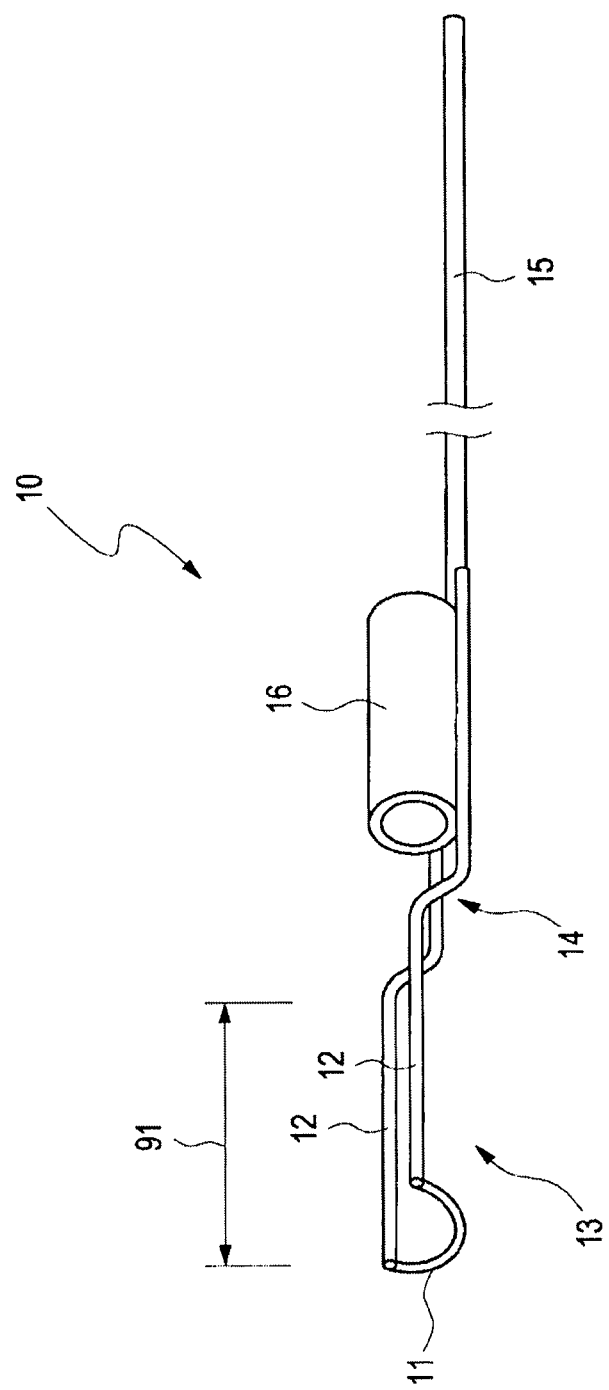
FIG. 3 shows a first illustrative embodiment of an electrode assembly according to the invention.

The electrode assembly 10 used in the resectoscope 1 according to FIG. 1, and corresponding to the one in FIG. 3, comprises a bipolar loop electrode 11 at its distal end. The loop electrode 11 is in this case arranged on the outer ends of two arms 12 of a fork assembly 13. The arms 12 of the fork assembly 13 are arranged on opposite sides of the optic 4 and thus also of the objective lens 5 (cf. section A-A in FIG. 1). By way of a transition region 14 with a reflexed airfoil profile, the two arms 12 of the fork assembly 13 are brought together to an electrode shaft 15. The electrode shaft 15 extends into the grip arrangement 3 and is there connected, on the one hand, to the grip element 3' for the described longitudinal displaceability and, on the other hand, to attachments (not shown) for the supply of high-frequency electrical energy. These attachments are configured according to the prior art.

For guiding the electrode assembly 10 in the region remote from the grip arrangement 3, a tubular guide element 16 is provided which is connected to the electrode shaft 15, adjacent to the transition region 14, and which engages completely around the optic 4 and can slide along the latter.

As will be seen from FIGS. 1 and 2, particularly from the sections A-A and B-B of FIG. 1, the electrode assembly 10 is arranged in the region between shaft tube 2 and optic 4 also used for the delivery of rinsing liquid. The transition region 14 of the electrode assembly 10 in particular causes swirling movements in the flow of rinsing liquid, which may be disadvantageous for rinsing free the viewing field of the optic 4 and of the objective lens 5. However, in the resectoscope 1 shown in FIGS. 1 and 2, the arms 12 of the fork assembly 13 are longer by more than 1.2 times the stroke length 90, such that, as is shown in FIG. 2, the transition region 14, even in the deployed state of the electrode assembly 10, is located far enough from the objective lens 5 to ensure that swirling movements in the flow of rinsing liquid caused by the transition region 14 have sufficiently settled again in the region of the objective lens 5, such that the viewing field of the optic 4 or of the objective lens 5 is quickly rinsed free if dirty. In the illustrative embodiment shown, the length 91 of the arms 12 of the fork assembly 13 measures 35 mm.

The illustrative embodiment of an electrode assembly 10 according to the invention shown in FIG. 3 has already been explained in connection with the resectoscope 1 from FIGS. 1 and 2, and therefore reference is made to the corresponding observations.

Figure 4:
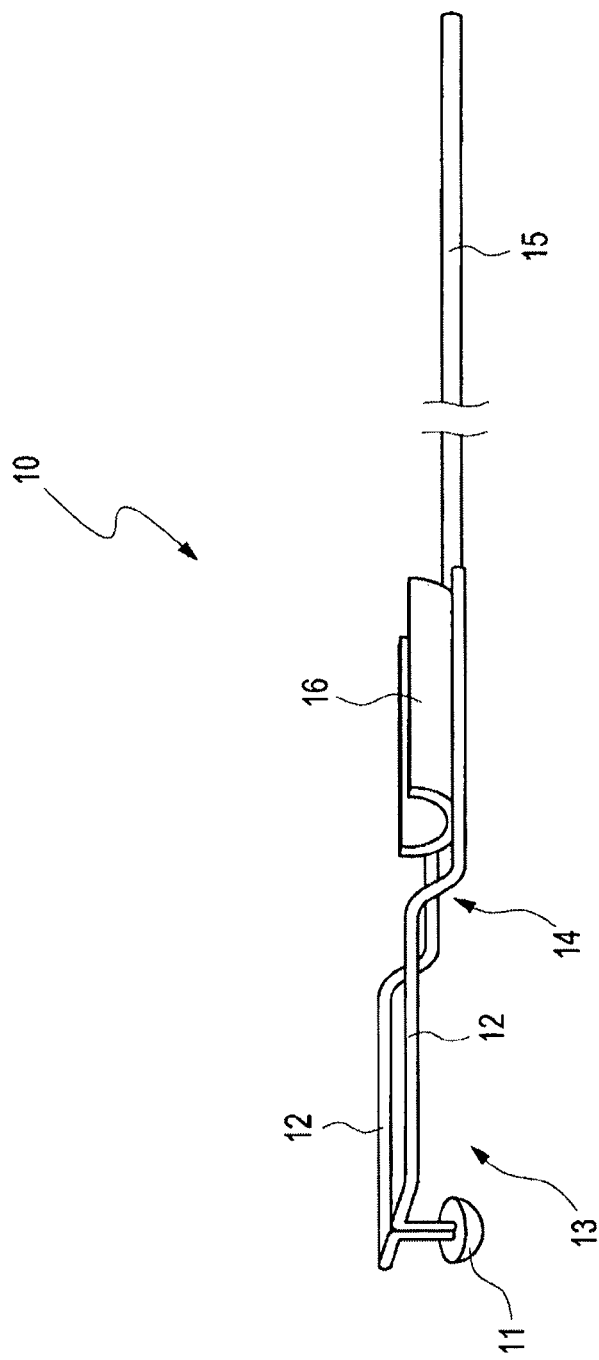
FIG. 4 shows a second illustrative embodiment of an electrode assembly according to the invention.

In FIG. 4 an alternative illustrative embodiment of an electrode assembly 10 according to the invention is shown. The basic design of the electrode assembly 10 with a fork assembly 13, a transition region 14 and an electrode shaft 15 corresponds here to that of the illustrative embodiment in FIG. 3. However, in the illustrative embodiment according to FIG. 4, the electrode 11 is by contrast configured as a flat vaporization electrode. In addition, the guide element is not a closed tubular element but instead has a cross section in the shape of a circular ring segment. The circular ring segment extends in this case through 220°, such that, for example in the resectoscope 1 according to FIGS. 1 and 2, the guide element 16 would engage around the optic by more than 60% of its circumference, as a result of which the electrode assembly 10 can be sufficiently guided on the optic 4.

The invention claimed is:

1. A resectoscope comprising:
   an elongate shaft tube, an elongate optic arranged therein with an objective lens at a distal end and with an electrode assembly,
   wherein the electrode assembly comprises an electrode arranged at a distal end of two arms of a fork assembly, which are arranged on opposite sides of the objective lens and are brought together in a transition region to an electrode shaft,
   wherein a guide element is provided on the electrode shaft, adjacent to the transition region, and interacts with the optic in such a way that that the electrode shaft is guided along the optic,
   wherein the electrode assembly is deployed in a longitudinal direction by a maximum stroke length from a fully retracted state, in which the electrode is arranged inside the shaft tube in front of the objective lens, to a fully deployed state, in which the arms of the fork assembly protrude from the shaft tube,
   wherein a length of the two arms of the fork assembly, which are arranged on opposite sides of the objective lens, is greater than 1.3 times the maximum stroke length.

2. The resectoscope as claimed in claim 1,
   wherein the transition region of the two arms of the fork assembly to the electrode shaft is designed in each case as a reflexed airfoil profile.

3. The resectoscope as claimed in claim 1,
   wherein the guide element is tubular.

4. The resectoscope as claimed in claim 1,
   wherein a region between the shaft tube and the optic is configured for rinsing liquid delivery.

5. The resectoscope as claimed in claim 1,
   wherein the shaft tube is double-walled, and a region between the walls of the shaft tube is configured for rinsing medium discharge.

6. The resectoscope as claimed in claim 1,
   wherein the electrode of the electrode assembly is a bipolar electrode.

7. The resectoscope as claimed in claim 1,
   wherein the maximum stroke length is 24 mm or the length of the two arms of the fork assembly is 30 mm to 28 mm.

8. An electrode assembly for use in a resectoscope, in which the electrode assembly is deployed in a longitudinal direction by a maximum stroke length from a fully retracted state to a fully deployed state, the electrode assembly comprising:
   an electrode arranged at a distal end of two arms of a fork assembly, which are arranged on opposite sides of an objective lens and are brought together in a transition region to an electrode shaft; and
   a guide element being provided on the electrode shaft, adjacent to the transition region, and interacting with an optic of the resectoscope in such a way that that the electrode shaft is guided along the optic,
   wherein a length of the two arms of the fork assembly, which are arranged on opposite sides of the objective lens, is greater than 1.3 times the maximum stroke length.

9. The electrode assembly as claimed in claim 8,
   wherein the electrode assembly is refined according to at least one of:
   the transition region of the two arms of the fork assembly to the electrode shaft is designed in each case as a reflexed airfoil profile,
   the guide element being tubular,
   the electrode of the electrode assembly being a bipolar electrode, and
   the maximum stroke length being 24 mm or the length of the two arms of the fork assembly being 30 mm to 28 mm.

\* \* \* \* \*